(12) United States Patent
Miriyala et al.

(10) Patent No.: US 12,316,370 B2
(45) Date of Patent: May 27, 2025

(54) ULTRASOUND TRANSMIT-RECEIVE SWITCH WITH COMBINED TRANSMIT-RECEIVE AND RETURN-TO-ZERO PATH

(71) Applicant: TEXAS INSTRUMENTS INCORPORATED, Dallas, TX (US)

(72) Inventors: Aravind Miriyala, Bengaluru (IN); Ravikumar Pattipaka, Bengaluru (IN); Raja Sekhar Kanakamedala, Bengaluru (IN); Sandeep Kesrimal Oswal, Bengaluru (IN)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 18/543,305

(22) Filed: Dec. 18, 2023

(65) Prior Publication Data

US 2024/0120962 A1    Apr. 11, 2024

Related U.S. Application Data

(62) Division of application No. 16/234,672, filed on Dec. 28, 2018, now Pat. No. 11,888,509.

(51) Int. Cl.
*H04B 1/44* (2006.01)
*B06B 1/02* (2006.01)
*H03K 17/00* (2006.01)
*H04B 11/00* (2006.01)
*A61B 8/00* (2006.01)
*A61B 8/14* (2006.01)

(52) U.S. Cl.
CPC .............. *H04B 1/44* (2013.01); *B06B 1/023* (2013.01); *H03K 17/00* (2013.01); *H03K 17/002* (2013.01); *H04B 11/00* (2013.01); *A61B 8/14* (2013.01); *A61B 8/54* (2013.01); *B06B 2201/76* (2013.01)

(58) Field of Classification Search
CPC .......... B06B 1/0238–0261; A61B 8/54; A61B 8/543546; H03K 17/002; H03K 17/005; H03K 17/007; H04B 1/44; H04B 1/00
See application file for complete search history.

(56) References Cited

U.S. PATENT DOCUMENTS

| | | | |
|---|---|---|---|
| 10,566,903 B1 | 2/2020 | Miller et al. | |
| 2014/0144240 A1* | 5/2014 | Barlow | B06B 1/0215 73/632 |
| 2014/0312954 A1* | 10/2014 | Ghisu | H03K 19/00361 327/333 |
| 2017/0310320 A1 | 10/2017 | Bottarel et al. | |

* cited by examiner

*Primary Examiner* — Patrick C Chen
(74) *Attorney, Agent, or Firm* — John R. Pessetto; Frank D. Cimino

(57) ABSTRACT

An ultrasound system includes a transmit-receive switch. The transmit-receive switch includes a combined transmit-receive and return-to-zero (RTZ) path. The combined transmit-receive and RTZ path includes a transistor with a first current terminal, a second current terminal, and a control terminal. The second current terminal of the transistor is coupled to a ground node via a first switch and is coupled to a receive node via a second switch. The ultrasound system also includes a receiver front-end circuit coupled to the receive node.

6 Claims, 3 Drawing Sheets

ULTRASOUND TRANSMIT-RECEIVE SWITCH WITH COMBINED TRANSMIT-RECEIVE AND RETURN-TO-ZERO PATH

CROSS-REFERENCE TO RELATED APPLICATIONS

This application is a division of U.S. patent application Ser. No. 16/234,672, filed Dec. 28, 2018, which application is hereby incorporated herein by reference.

BACKGROUND

Ultrasonic imaging has become widely used in medical and/or other applications. In an example ultrasound technique, a controller and driver circuit drives an acoustic transducer to introduce high-frequency acoustic waves into a subject's body, where the materials in the subject's body have different reflection coefficients resulting in echoes of these acoustic waves. The same acoustic transducer converts the echoes into electrical signals. By gathering echoes associated with different depths of investigation and/or angles, 2D or 3D depth images of the subject's body are generated.

To obtain a clear image, a high signal-to-noise ratio (SNR) is desirable to overcome random noise associated with the imaging process, One way to increase the SNR is to increase the amplitude of the signal driving the transducer. In some examples, the transducer drive signal may require voltages in the range of +/−75 volts to +/−100 volts. Also, in some ultrasonic systems, the process of transmitting and receiving acoustic signals involves a transmit-receive switch that controls when the transducer is coupled to a transmitter circuit or to a receiver circuit. The timing and switching artifacts related the transmit-receive switch affects the availability of near field data and the SNR for an ultrasonic system.

SUMMARY

In accordance with at least one example of the disclosure, an ultrasound system comprises a transmit-receive switch. The transmit-receive switch comprises a combined transmit-receive and return-to-zero (RTZ) path. The combined transmit-receiver and RTZ path comprises a transistor with a first current terminal, a second current terminal, and a control terminal. The second current terminal of the transistor is coupled to a ground node via a first switch and is coupled to a receive node via a second switch. The ultrasound system also comprises a receiver front-end circuit coupled to the receive node.

In accordance with at least one example of the disclosure, gate drive control circuitry comprises a first transistor and a second transistor of a combined transmit-receive and RTZ path. The gate drive control circuitry comprises a gate-on drive control circuit for the second transistor. The gate-on drive control circuit comprises: 1) a third transistor with a first current terminal, a second current terminal, and a control terminal; 2) a fourth transistor with a first current terminal, a second current terminal, and a control terminal; 3) a first diode with an anode coupled to the second current terminal of the third transistor and with a cathode coupled to the first current terminal of the fourth transistor; and 4) a second diode with an anode coupled to a transmit node and with a cathode coupled to the first current terminal of the fourth transistor, and wherein a second current terminal of the fourth transistor is coupled to the control terminal of the second transistor.

In accordance with at least one example of the disclosure, a transmit and receive switch comprises a transmit node and a receive node. The transmit and receive switch also comprises a first transistor with a first current terminal, a second current terminal, and a control terminal, wherein the second current terminal of the first transistor is coupled to a ground node via a first switch and is coupled to the receive node via a second switch. The transmit and receive switch also comprises a second transistor with a first current terminal, a second current terminal, and a control terminal, wherein the first current terminal of the second transistor is coupled to the transmit node, and wherein the second current terminal of the second transistor is coupled to the first current node of the first transistor. The transmit and receive switch also comprises a controller configured to provide control signals to the control terminal of the first transistor, the control terminal of the second transistor, the first switch, and the second switch based on a transmit mode, a receive mode, and a return-to-zero (RTZ) mode.

BRIEF DESCRIPTION OF THE DRAWINGS

For a detailed description of various examples, reference will now be made to the accompanying drawings in which.

DETAILED DESCRIPTION

Disclosed herein are transmit-receive switch topologies and related systems and methods, where the disclosed transmit-receive switch topologies involve a combined transmit-receive and return-to-zero (RTZ) path. In some examples, the combined transmit-receive and RTZ path includes a first transistor with a first current terminal, a second current terminal, and a control terminal, where the second current terminal of the first transistor is coupled to a ground node via a first switch and is coupled to a receive node via a second switch. In addition, the combined transmit-receive and RTZ path includes a second transistor with a control terminal, a first current terminal, and second current terminal, where second current terminal of the second transistor is coupled to the first current terminal of the first transistor. Also, the first current terminal of the second transistor is coupled to a transmit node. To direct different operations of the transmit-receive switch, a controller is configured to provide control signals to the control terminal of the first transistor, the control terminal of the second transistor, the first switch, and the second switch, where the control signals are based on a transmit mode, a receive mode, and an RTZ mode.

In some examples, the disclosed transmit-receive switch devices, systems, and methods are used in an ultrasound scenario. In such case, the transmit-receive switch directs operations of the combined transmit-receive and RTZ path to cause the transmit node to transition from a neutral voltage level to a positive transducer driver voltage level, to transition from the positive transducer driver voltage level to the neutral voltage level (an RTZ transition), to transition from the neutral voltage level to a negative transducer driver voltage level, and to transition from the negative transducer driver voltage level to the neutral voltage level (another RTZ transition). As desired, when the transmit node is at the neutral voltage, the transmit-receive switch also directs the combined transmit-receive and RTZ path to couple the transmit node to a receive node.

In at least some examples of the disclosed transmit-receive switch topologies, switching between a transmit mode and a receive mode is sufficiently fast to support near field imaging of ultrasound equipment. Also, in some examples, transitions (e.g., neutral-to-high, high-to-neutral, neutral-to-low, low-to-neutral, transmit mode to receive mode) related to the combined transmit-receive and RTZ path topologies comply with a minimal artifact criterion. With the disclosed transmit-receive switch topologies, the size of the transmit-receive switch is strategically reduced to lower cost and the footprint. To provide a better understanding, various transmit-receive switch options and controller options are described using the figures as follows.

Figure 1:
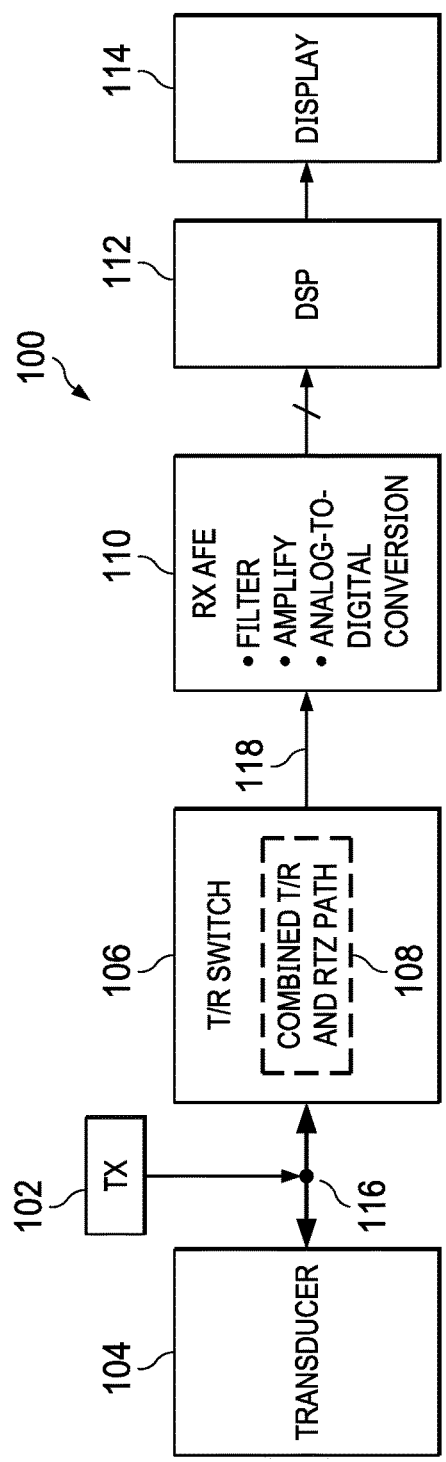
FIG. 1 is a block diagram showing a system in accordance with various examples.

FIG. 1 is a block diagram showing a system 100 in accordance with various examples. In some examples, the system 100 represents ultrasound equipment or other imaging equipment configured to transmit signals, receive echoes, process echo data (e.g., compare echo data with baseline data), and generate images based on the processed echo data (e.g., the comparison results). As shown, the system 100 includes a transmitter (TX) circuit 102 coupled to a transducer 104. In the example of an ultrasound system, the transducer 104 is an acoustic transducer that responds to electrical signals from the TX circuit 102 by generating high-frequency acoustic signals (e.g., in the range of 1-20 Mhz). The transducer 104 also responds to received acoustic signals (e.g., echoes or reflected signals resulting from a transmitted signal) by generating electrical signals.

In the system 100, a transmit-receive (T/R) switch 106 is positioned between a transmit node 116 and a receive node 118, where signals at the transmit node 116 at a given time are due to the operations of the TX circuit 102 and/or the transducer 104. In operation, the T/R switch 106 selectively passes whatever signal is at the transmit node 116 to the receive node 118. More specifically, in the disclosed examples, the T/R switch 106 includes a combined T/R and RTZ path 108 to selective pass whatever signals is at the transmit node 116 to the receive node 118. Also, the combined T/R and RTZ path 108 is used to ground a positive or negative signal (e.g., a positive or negative transducer driver voltage level) provided by the TX circuit 102 before the receive node 106 is coupled to the transmit node (to quiet the signal at the transmit node 116 before receive operations begin).

In system 100, transmit operations are performed while the T/R switch 106 is turned off with regard to coupling the transmit node 116 and the receive node 118. Example transmit operations involve the TX circuit 102 providing a positive transducer driver signal followed by a negative transducer driver signal, or vice versa. Even through the T/R switch 106 is turned off with regard to coupling the transmit node 116 and the receive node 118, the combined T/R and RTZ path 108 enables the T/R switch 106 to perform RTZ operations to ground the transmit node 116 as desired (e.g., after a positive transducer driver signal or after a negative transducer driver signal).

In system 100, receive operations are performed while the T/R switch 106 is turned on with regard to coupling the transmit node 116 and the receive node 118. During receive operations, an ultrasound or receiver (RX) analog front-end circuit (AFE) 110 performs operations such as signal filtering, signal amplification, and analog-to-digital conversion. To perform such operations, the RX AFE 110 includes a filter circuit, an amplifier circuit, and an analog-to-digital converter (ADC). The digitized signals output from the RX AFE are provided to a digital signal processor (DSP) 112 configured to perform signal processing on the digitized signals (e.g., comparing echo signal data with baseline data). In system 100, the operations of the DSP 112 result in image data (e.g., a 2D or 3D image of a subject's internal organs), where the image data is presented on a display 114.

Figure 2:
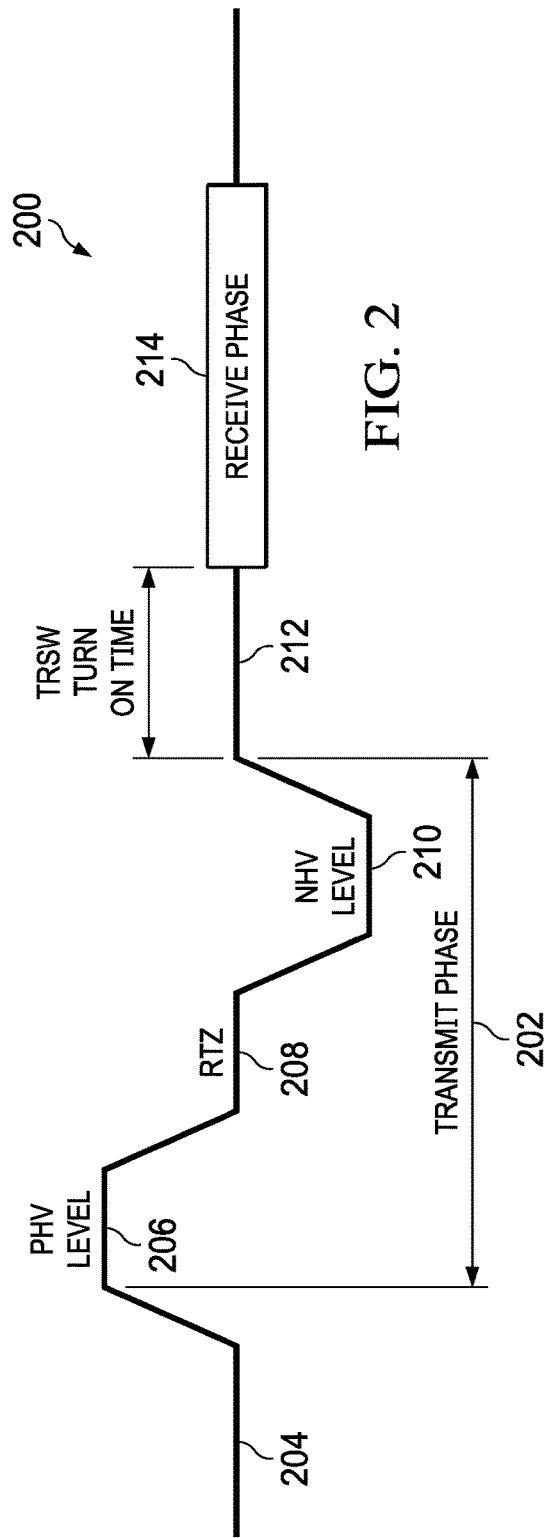
FIG. 2 is a block diagram showing a transmit and receive sequence in accordance with various examples.

FIG. 2 is a block diagram showing a transmit and receive sequence 200 in accordance with various examples. In some examples, the transmit and receive sequence 200 is performed using a T/R switch (e.g., the T/R switch 106 in FIG. 1) with a combined T/R and RTZ path (e.g., the combined T/R and RTZ path 108). More specifically, a T/R switch directs operations of a combined transmit-receive and RTZ path (e.g., the combined T/R and RTZ path 108), which cause a transmit node (e.g., the transmit node 116) to transition from a first neutral voltage level 204 to a positive high-voltage (PHV) (e.g., a positive transducer driver voltage) level 206, to transition from the positive transducer driver voltage level 206 to a second neutral voltage level 208 (an RTZ transition), to transition from the second neutral voltage level 208 to a negative high-voltage (NHV) (e.g., a negative transducer driver voltage) level 210, and to transition from the negative transducer driver voltage level 210 to a third neutral voltage level 212 (another RTZ transition).

In some examples, a transmit phase 202 (e.g., an ultrasound transmit phase) includes at least part of the PHV level 206, the second neutral voltage level 208, and at least part of the NHV level 210. Later, a receive phase 214 begins after the transmit phase 202 ends, wherein the receive phase 214 occurs after a T/R switch is turned on (to couple the transmit node 116 and the receive node 118). As shown, the receive phase 214 begins after a third neutral voltage level 212 has started (when the transmit node 116 has settled after the transmit phase 202). For example, in an ultrasound scenario, the receive phase 214 is used to monitor and interpret echoes resulting from the transmit phase 202.

Figure 3:
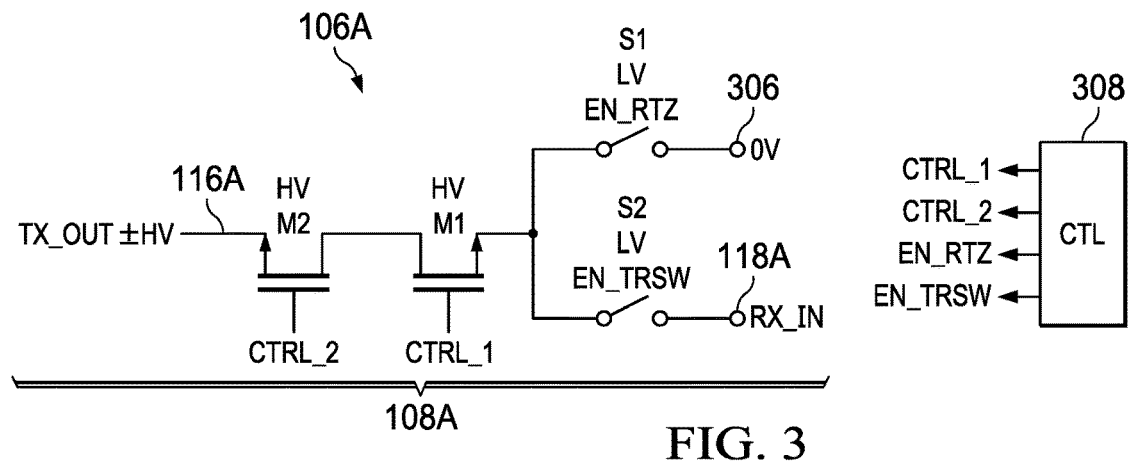
FIG. 3 is a schematic diagram showing a transmit-receive switch in accordance with various examples.

FIG. 3 is a schematic diagram showing a transmit-receive switch 106A (an example of the transmit-receive switch 106 in FIG. 1) in accordance with various examples. As shown, the transmit-receive switch 106A includes combined transmit-receive and RTZ path 108A and a controller 308. More specifically, the combined transmit-receive and RTZ path 108A includes a first transistor (M1) and a second transistor (M2), each having a respective control terminal, first current terminal, and second current terminal.

As shown, the first current terminal of M2 is coupled to a transmit node 116A (an example of the transmit node 116 in FIG. 1), and the second current terminal of M2 is coupled to the first current terminal of M1. Meanwhile, the second current terminal of M1 is coupled to a ground node 306 via a first switch, S1. Also, the second current terminal of M1 is coupled to a receive node 118A (an example of the receive node 118 in FIG. 1) via a second switch, S2. In at least some examples, M1 and M2 are high-voltage (HV) transistors, and S1 and S2 are low-voltage (LV) switches. In one example, M1 and M2 operate at voltages in excess of ±75V and are sized for a transducer drive current (e.g., 2 amps to drive the transducer 104 in FIG. 1), while S1 and S2 operate at voltages of +5V or less and using currents that are much less than a transducer drive current.

The control signals for M1, M2, S1, and S2 are provided by the controller 308, and depend on whether the combined transmit-receive and RTZ path 108A is being operated in a transmit mode, an RTZ mode, or a receive mode. In FIG. 3, the control signal for M1 is labeled CTRL_1, the control signal for M2 is labeled CTRL_2, the control signal for S1 is labeled EN_RTZ, and the control signal for S2 is labeled EN_TRSW. In a transmit mode (e.g., when the transmit node 116A is at the PHV level 206 or the NHV level 210 in FIG. 2), CTRL_1 is a logical "0" and CTRL_2 is a logical "0" to decouple the transmit node 116A from the receive node 118A. In an RTZ mode, CTRL_1 is a logical "1" and CTRL_2 is a logical "1", EN_RTZ is a logical "1", and EN_TRSW is a logical "0" to ground the transmit node 116A (e.g., to cause the transmit node 116A to transition to the neutral voltage level 208 in FIG. 2). In a receive mode, CTRL_1 is a logical "1" and CTRL_2 is a logical "1", EN_RTZ is a logical "0", and EN_TRSW is a logical "1" to couple the transmit node 116A to the receive node 118A.

In the example of FIG. 3, M1 includes a source terminal, a drain terminal, and a gate terminal, where the source terminal of M1 is coupled to the ground node 306 via a first switch (S1) and is coupled to the receive node 118A via a second switch (S2). Meanwhile, M2 includes a source terminal, a drain terminal, and a gate terminal, where the source terminal of M2 is coupled to the transmit node 116A, and wherein the drain terminal of M2 is coupled to the drain terminal of M1. In some examples, M1 and M2 are configured to handle voltages of 75V or more. Meanwhile, S1 and S2 are configured to handle voltages of 5V or less.

Figure 4:
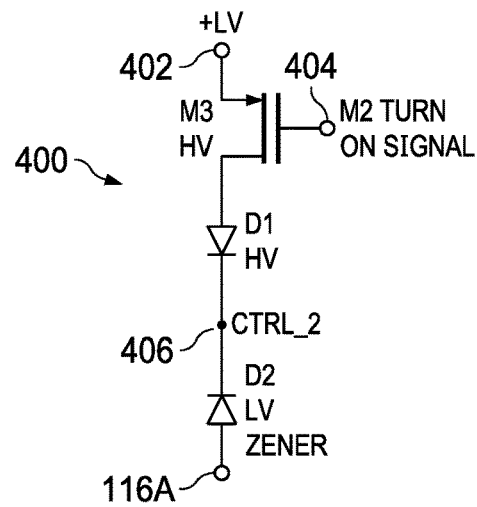
FIG. 4 is a schematic diagram showing a controller circuit for a transmit-receive switch in accordance with various examples.

FIG. 4 is a schematic diagram showing a controller circuit 400 for a transmit-receive switch in accordance with various examples. In some examples, the controller circuit 400 is part of the controller 308 represented in FIG. 3. More specifically, the controller circuit 400 represents a gate-on drive control circuit configured to provide a CTRL_2 "turn on" signal. As shown, the controller circuit 400 comprises a transistor (M3) with a first current terminal, a second current terminal, and a control terminal. In some examples, M3 is sized for a current that is much less than a transducer drive current (e.g., if the transducer drive current is 2 amps, M3 is sized for 100 mA). The first current terminal of M3 is coupled to a power supply node 402 configured to provide +LV (a positive low-voltage level such as +5V or less). The second current terminal of M3 is coupled to the anode of a first diode (D1). The cathode of D1 is coupled to the cathode of a second diode (D2, a Zener diode). The anode of D2 is coupled to the transmit node 116A. In the controller circuit 400, D1 can handle a high-voltage level such as 150V. As shown, the control terminal for M3 selectively receives an M2 "turn on" signal at node 404. In response to the M2 "turn on" signal at node 404 being a logical "1", a node 406 between D1 and D2 goes high, resulting in CTRL_2 being a logical "1", resulting in M2 being turned on.

Figure 5:
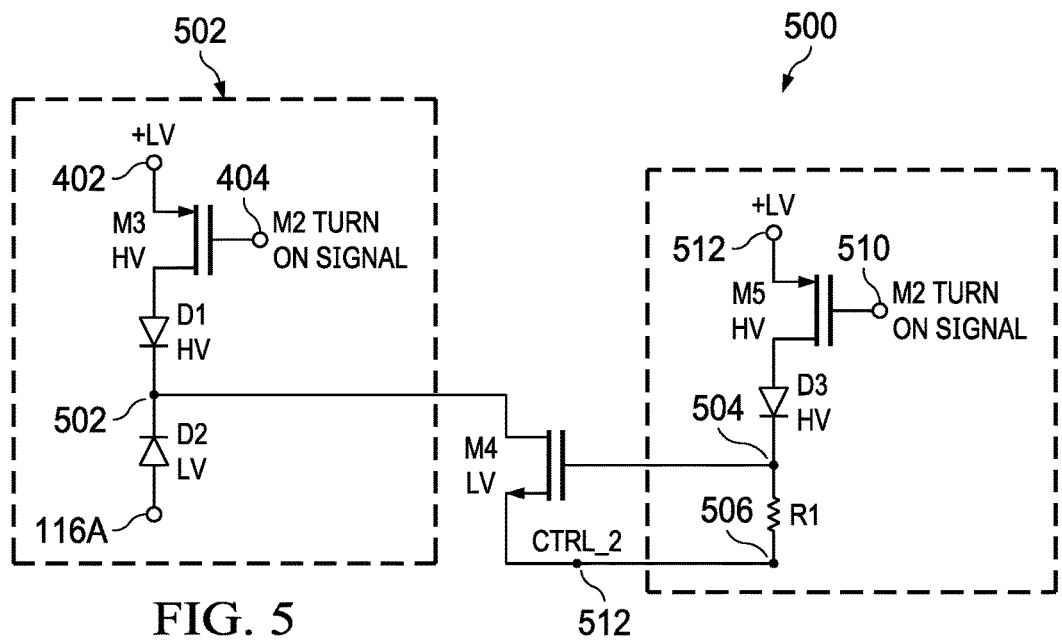
FIG. 5 is a schematic diagram showing another controller circuit for a transmit-receive switch in accordance with various examples.

FIG. 5 is a schematic diagram showing another controller circuit 500 for a transmit-receive switch in accordance with various examples. In some examples, the controller circuit 500 is part of the controller 308 represented in FIG. 3, where the controller circuit 500 is an alternative to the controller circuit 400 of FIG. 4, where the controller circuit 500 represents a gate-on drive control circuit configured to provide the CTRL_2 "turn on" signal. In the controller circuit 500 various components introduced for the controller circuit 400 are represented as circuit 502. More specifically, the circuit 502 comprises M3, where the first current terminal of M3 is coupled to the power supply node 402, which provides +LV (a positive low-voltage level such as +5V or less). Meanwhile, the control terminal of M3 is coupled to a node 404 configured to provide an M2 "turn on" signal. Also, the second current terminal of M3 is coupled to the anode of D1. The cathode of D1 is coupled to the cathode of a D2. The anode of D2 is coupled to the transmit node 116A. As previously discussed for the controller circuit 400, D1 can handle a high-voltage level such as 150V.

The controller circuit 500 includes additional components compared to the controller circuit 400 or circuit 502. As shown, the controller circuit 500 also includes two additional transistors (M4 and M5), each with a respective first current terminal, second current terminal, and control terminal. More specifically, the first current terminal of M5 is coupled to a power supply node 512 configured to provide a low-voltage power supply (e.g., 5V or less). In some examples, M5 is sized to operate with currents that are much less than a transducer drive current (e.g., if the transducer driver current is 2 amps, then M5 is sized for a current of 100 mA). The control terminal of M5 is coupled to a node 510 configured to provide an M2 "turn on" signal. Meanwhile, the second current terminal of M5 is coupled to the anode of a third diode (D3) sized to handle a high-voltage level (e.g., 150V). The cathode of D3 is coupled to first side of a resistor (R1), where the second side of R1 is coupled to a second current terminal of M4. As shown, the first current terminal of M4 is coupled to a node 506 between D1 and D2. Also, the control terminal of M4 is coupled to a node 504 between D3 and R1. In some examples, M4 is sized to operate with currents that are much less than a transducer drive current (e.g., if the transducer driver current is 2 amps, then M4 is sized for a current of 100 mA). For the controller circuit 500, a node 512 between the second side of R1 and the second current terminal of M4 provides CTRL_2. In other words, when an M2 "turn on" signal is applied to the control terminals of M3 and M5, the node 512 corresponding to CTRL_2 is at a logical "1", resulting in M2 being turned on. With the controller circuit 500, the gate control is isolated from D2.

In some examples, a TX_OUT signal (e.g., to drive the transducer 104) is between +100V and −100V and switches quickly. In order to turn M2 on, a floating bias of 5V is applied to CTRL_2 with reference to TX_OUT. In one example of the controller circuit 400, M2 is turned on by placing a 5V zener diode (e.g., D2) between CTRL_2 and TX_OUT. Also, current is pumped into CTRL_2 when a transmit-receive switch needs to be turned on. In such case, the 5V Zener diode (e.g., D2) breaks down and limits Vgs to the zener voltage. Because the zener diode (e.g., D2) may take certain amount of time to recover from zener breakdown region, a constraint on the turn off time exists. To avoid this constraint, an alternative CTRL_2 turn on controller circuit such as the controller circuit 500 added one NMOS LV switch (e.g., M4) to isolate CTRL_2 from TX_OUT+the Zener reverse break down voltage (e.g., 5V).

Figure 6:
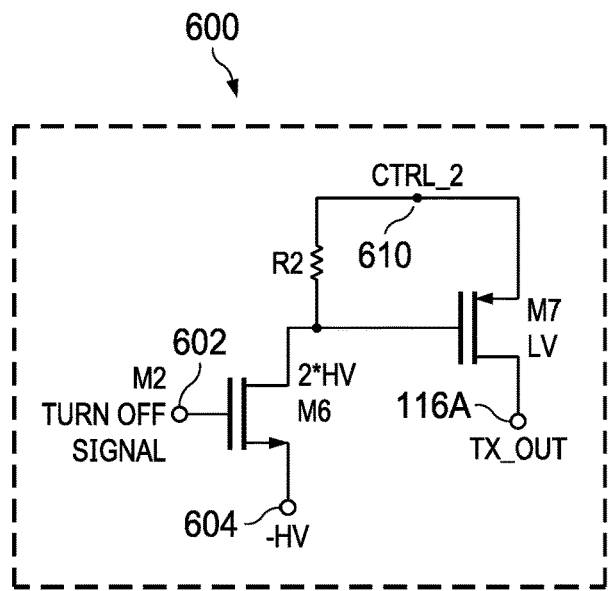
FIG. 6 is a schematic diagram showing another controller circuit for a transmit-receive switch in accordance with various examples.

FIG. 6 is a schematic diagram showing another controller circuit 600 for a transmit-receive switch in accordance with various examples. In some examples, the controller circuit 600 is part of the controller 308 represented in FIG. 3, where the controller circuit 600 represents a gate-off drive control circuit configured to provide a CTRL_2 "turn off" signal. As shown, the controller circuit 600 includes two transistors (M6 and M7), each having a respective control terminal, first current terminal, and second current terminal. More specifically, the second current terminal of M6 is coupled to a node 604 configured to provide a negative high-voltage level (e.g., −100V). The first current terminal of M6 is coupled to the control terminal of M7. Meanwhile, the second current terminal 116A of M7 is coupled to the transmit node 116A. Also, the first current terminal of M7 is coupled to a first side of a resistor, R2, while the second side of R2 is coupled to the control terminal of M7 and the first current terminal of M6. In some examples, M6 and M7 are each sized to operate with currents that are much less than a transducer drive current (e.g., if the transducer driver current is 2 amps, then M6 and M7 are each sized for a current of 100 mA). When an M2 "turn off" signal is provided to the control terminal of M6, the CTRL_2 signal at node 610 (between the first side of R2 and the first current terminal of M7) is a logical "0", resulting in M2 being turned off.

In some examples, CTRL_2 is shorted to the transmit node 116A (shorted to TX_OUT) in order to turn off M2. As represented in the controller circuit 600, this is done by placing a low-voltage PMOS switch (e.g., M7) between CTRL_2 and the transmit node 116A (TX_OUT). Also, a floating bias of 5V is generated with reference to CTRL_2 and is applied to the gate of the PMOS switch (e.g., M7).

Figure 7:
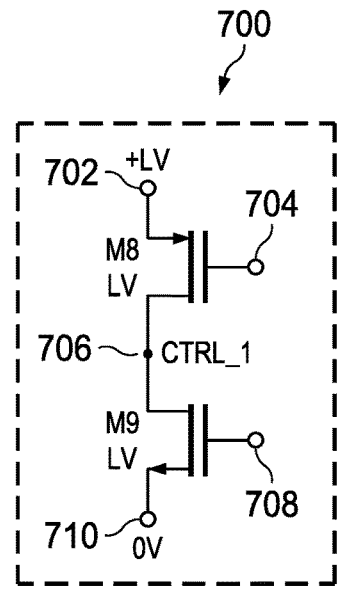
FIG. 7 is a schematic diagram showing another controller circuit for a transmit-receive switch in accordance with various examples.

FIG. 7 is a schematic diagram showing another controller circuit 700 for a transmit-receive switch in accordance with various examples. In some examples, the controller circuit 700 is part of the controller 308 represented in FIG. 3, where the controller circuit 700 represents a gate-on-off drive control circuit configured to provide CTRL_1 "turn on" and "turn off" signals. As shown, the controller circuit 700 includes two transistors, M8 and M9, where each includes a respective control terminal, first current terminal, and second current terminal. More specifically, the first current terminal of M8 is coupled to node 702 configured to provide a low-voltage level (e.g., a value much less than the transducer drive voltage level such as a value of +5V or less). The second current terminal of M8 is coupled to the first current terminal of M9. Meanwhile, the second current terminal of M9 is coupled to a ground node 710. In some examples, M8 and M9 are each sized to operate with currents that are much less than a transducer drive current (e.g., if the transducer driver current is 2 amps, then M8 and M9 are each sized for a current of 100 mA). In operation, the signal at node 706 (between the second current terminal of M8 and the first current terminal of M9) is used as CTRL_1, where the value of CTRL_1 depends on the control signal for M8 at node 704, and the control signal for M9 at node 708. More specifically, if M8 is on and M9 is off, CTRL_1 will be a logical "1", resulting in M1 being turned on. On the other hand, if M8 is off and M9 is on, CTRL_1 will be a logical "0" resulting in M1 being turned off. As represented for the controller circuit 700, generation of CTRL_1 is direct because it needs +5V to turn ON and 0V to turn OFF.

Figure 8:
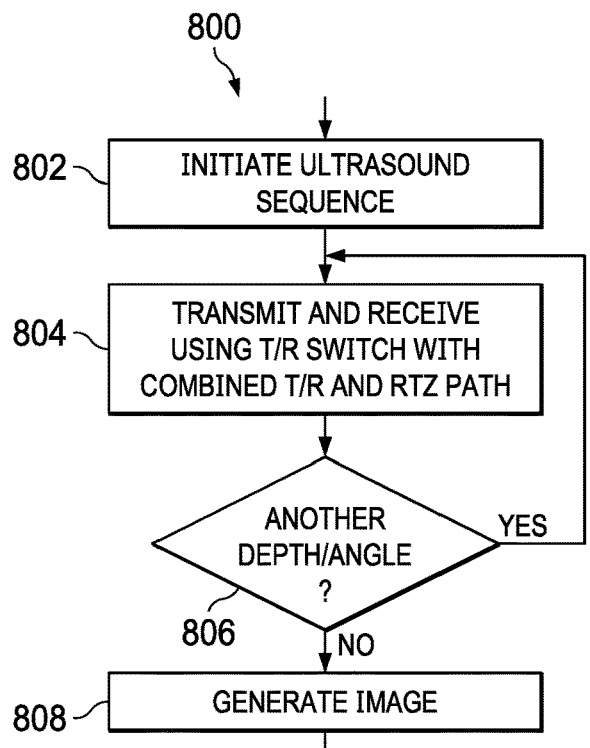
FIG. 8 is a block diagram showing an ultrasound method in accordance with various examples.

FIG. 8 is a block diagram showing an ultrasound method 800 in accordance with various examples. In the method 800, an ultrasound sequence is initiated at block 802. At block 804, transmit and receive operations are performed using a transmit-receiver switch (e.g., the transmit-receiver switch 106 in FIG. 1, or the transmit-receive switch 106A in FIG. 2) with a combined transmit-receive and RTZ path (e.g., the combined transmit-receive and RTZ path 108 of FIG. 1, or the combined transmit-receive and RTZ path 108A of FIG. 2). In some examples, the operations of block 804 includes the transmit and receive sequence 200 of FIG. 2. If another depth/angle is needed (determination block 806), the operations of block 804 are repeated, where another frequency or angle is used to vary the depth or angle of information received. If another depth/angle is not needed (determination block 806), the method 800 generates an image based on the transmit and receive operations of block 804.

With the disclosed transmit-receive switch topologies, transmit-receiver switch and RTZ components are combined to improve area efficiency compared to other transmit-receive switch topologies. Also, the disclosed transmit-receive switch topologies provide fast switching to support near field imaging. In some examples, the "turn on" time for the disclosed transmit-receive switch topologies is less than 100 ns. In some examples, the fast "turn on" or "turn off" times are achieved using the controller circuits 400, 500, 600, and/or 700 described herein in FIGS. 4-7. Also, "turn on" and "turn off" operations of the disclosed transmit-receive switch topologies result in minimal output transients (minimal secondary transmits). For RTZ operations, the disclosed transmit-receive switch topologies pull the transmit node to proper 0V instead of a residual voltage, which helps to ensure minimal secondary transmits. With the disclosed transmit-receive switch topologies, area efficiency is achieved, resulting in lower cost and smaller chip size. In some examples, the disclosed transmit-receive switch topologies includes a combined transmit-receive and RTZ path that uses two high-voltage NMOS switches instead of 1 high-voltage PMOS and three high-voltage NMOS switches used in another example transmit-receive switch topology.

Certain terms have been used throughout this description and claims to refer to particular system components. As one skilled in the art will appreciate, different parties may refer to a component by different names. This document does not intend to distinguish between components that differ only in name but not in their respective functions or structures. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A transmit and receive switch, comprising:
 a first transistor with a first current terminal, a second current terminal, and a control terminal, wherein the second current terminal of the first transistor is coupled to a ground via a first switch and is coupled to a receive node via a second switch;
 a second transistor with a first current terminal, a second current terminal, and a control terminal, wherein the first current terminal of the second transistor is coupled to a transmit terminal, and wherein the second current terminal of the second transistor is coupled to the first current terminal of the first transistor; and a controller configured to provide control signals to the control terminal of the first transistor, the control terminal of the second transistor, the first switch, and the second switch based on a transmit mode, a receive mode, and a return-to-zero (RTZ) mode;

wherein the controller is further configured to use the transmit mode to change the transmit terminal from a neutral voltage level to a positive transducer driver voltage level, wherein the controller is further configured to use the RTZ mode to change the transmit terminal from the positive transducer driver voltage to a neutral voltage level, wherein the controller is further configured to use the transmit mode to change the transmit terminal from a neutral voltage level to a negative transducer driver voltage level, wherein the controller is further configured to use the RTZ mode to change the transmit node from the negative transducer driver voltage to a neutral voltage level, and wherein the controller is further configured to use the receive mode while the transmit terminal is at a neutral voltage level.

2. The transmit and receive switch of claim 1, wherein the controller further comprises a gate-on drive control circuit for the second transistor, wherein the gate-on drive control circuit comprises:
  a third transistor with a first current terminal, a second current terminal, and a control terminal;
  a first diode with an anode coupled to the second current terminal of the third transistor and with a cathode coupled to the control terminal of the second transistor; and
  a second diode with an anode coupled to a transmit node and with a cathode coupled to the control terminal of the second transistor.

3. The transmit and receive switch of claim 1, wherein the controller further comprises a gate-on drive control circuit for the second transistor, wherein the gate-on drive control circuit comprises:
  a third transistor with a first current terminal, a second current terminal, and a control terminal;
  a fourth transistor with a first current terminal, a second current terminal, and a control terminal;
  a first diode with an anode coupled to the second current terminal of the third transistor and with a cathode coupled to the first current terminal of the fourth transistor; and
  a second diode with an anode coupled to a transmit node and with a cathode coupled to the first current terminal of the fourth transistor, and wherein a second current terminal of the fourth transistor is coupled to the control terminal of the second transistor.

4. The transmit and receive switch of claim 3, wherein the gate-on drive control circuit further comprises:
  a fifth transistor with a first current terminal, a second current terminal, and a control terminal;
  a third diode with an anode coupled to the second current terminal of the fifth transistor;
  a resistor with a first terminal and a second terminal, wherein the first terminal of the resistor is coupled a cathode of the third diode, and wherein the second terminal of the resistor is coupled to the control terminal of the second transistor.

5. The transmit and receive switch of claim 4, wherein the resistor is a first resistor, wherein the controller further comprises a gate-off drive control circuit for the second transistor, and wherein the gate-off drive control circuit comprises:
  a sixth transistor with a first current terminal, a second current terminal, and a control terminal, wherein the second current terminal of the sixth transistor is coupled to a negative transducer drive voltage node;
  a seventh transistor with a first current terminal, a second current terminal, and a control terminal, wherein the first current terminal of the seventh transistor is coupled to the control terminal of the second transistor; and
  a second resistor with a first terminal coupled to the first current terminal of the seventh transistor and with a second terminal coupled to the control terminal of the seventh transistor and to the first current terminal of the sixth transistor.

6. The transmit and receive switch of claim 5, wherein the controller further comprises a gate-on-off drive control circuit for the first transistor, and wherein the gate-on-off drive control circuit comprises:
  an eighth transistor with a first current terminal, a second current terminal, and a control terminal, wherein the first current terminal of the eighth transistor is coupled to a voltage supply configured to provide a voltage below a transducer driver voltage level; and
  a ninth transistor with a first current terminal, a second current terminal, and a control terminal, wherein the second current terminal of the ninth transistor is coupled to ground, and wherein control terminal of the first transistor is coupled to first current terminal of the ninth transistor and to the second current terminal of the eighth transistor.

* * * * *